US012558479B2

(12) United States Patent
Van Antwerp et al.

(10) Patent No.: US 12,558,479 B2
(45) Date of Patent: Feb. 24, 2026

(54) SENSOR CANNULA

(71) Applicant: LAXMI THERAPEUTIC DEVICES, INC., Goleta, CA (US)

(72) Inventors: William Peter Van Antwerp, Santa Clarita, CA (US); Drew Amaral, Santa Margarita, CA (US); Thomas Metzmaker, Goleta, CA (US)

(73) Assignee: LAXMI THERAPEUTIC DEVICES, INC., Goleta, CA (US)

( * ) Notice: Subject to any disclaimer, the term of this patent is extended or adjusted under 35 U.S.C. 154(b) by 0 days.

(21) Appl. No.: 18/920,568

(22) Filed: Oct. 18, 2024

(65) Prior Publication Data

US 2025/0127984 A1 Apr. 24, 2025

Related U.S. Application Data

(60) Provisional application No. 63/592,067, filed on Oct. 20, 2023.

(51) Int. Cl.
*A61B 5/05* (2021.01)
*A61B 5/00* (2006.01)
(Continued)

(52) U.S. Cl.
CPC ......... *A61M 5/158* (2013.01); *A61B 5/14532* (2013.01); *A61B 5/1473* (2013.01);
(Continued)

(58) Field of Classification Search
CPC ............ A61B 5/14532; A61B 5/14865; A61B 5/14546; A61B 5/4839; A61B 5/1495; A61B 5/1473; A61B 5/1486; A61B 5/14503; A61B 5/6833; A61B 5/6801; A61B 5/389; A61B 5/6802; A61B 5/150503; A61B 5/026; A61B 5/036; A61B 5/685; A61B 5/150984; A61B 5/0531; A61B 5/14535; A61M 5/1723; A61M 2230/201; A61M 5/14; A61M 5/158;
(Continued)

(56) References Cited

U.S. PATENT DOCUMENTS

| | | | |
|---|---|---|---|
| 8,688,237 B2 * | 4/2014 | Stanislaus | A61B 1/267 607/124 |
| 2003/0069613 A1 * | 4/2003 | Kuzma | A61B 17/1679 607/40 |

(Continued)

OTHER PUBLICATIONS

International Search Report and Written Opinion for Application No. PCT/US2024/052119, mailed Jan. 14, 2025, 9 pages.

*Primary Examiner* — Joseph A Stoklosa
*Assistant Examiner* — Brian M Antiskay
(74) *Attorney, Agent, or Firm* — Womble Bond Dickinson (US) LLP

(57) ABSTRACT

A sensor assembly includes a body having a first end, a second end, and a longitudinal axis extending between the first and second ends, wherein at least part of the body is tubular and defines a cavity that extends along the longitudinal axis to facilitate delivery of medication therethrough, and a plurality of electrodes formed on a surface of the body, wherein each of the electrodes extends at least partially longitudinally along the body, with an electrical contact closer to the first end and a sensing region closer to the second end.

17 Claims, 6 Drawing Sheets

(51) Int. Cl.
*A61B 5/145*     (2006.01)
*A61B 5/1473*    (2006.01)
*A61M 5/142*     (2006.01)
*A61M 5/158*     (2006.01)
*A61M 5/172*     (2006.01)

(52) U.S. Cl.
CPC ....... *A61B 5/6848* (2013.01); *A61M 5/14248*
(2013.01); *A61M 2005/1726* (2013.01); *A61M*
*2205/3317* (2013.01); *A61M 2230/201*
(2013.01)

(58) Field of Classification Search
CPC ...... A61M 2005/1585; A61M 5/14248; A61M
37/00; A61M 37/0015; A61M 2037/0023;
A61M 2005/14252; A61M 2005/14268;
A61M 2037/0007; A61M 2037/003;
A61M 2037/0046; A61M 2037/0061;
G16H 20/17
USPC ........ 600/301, 308, 316, 325–327, 345–347,
600/354, 372–373, 377, 382, 384, 386,
600/391, 393
See application file for complete search history.

(56)                References Cited

U.S. PATENT DOCUMENTS

| 2008/0214916 | A1  |  9/2008 | Yodfat et al. |            |
|--------------|-----|---------|---------------|------------|
| 2010/0113907 | A1* |  5/2010 | Schwind ..............  | A61B 5/6849 |
|              |     |         |               | 600/345    |
| 2010/0274112 | A1* | 10/2010 | Hoss ................... | A61M 5/1723 |
|              |     |         |               | 600/347    |
| 2012/0310067 | A1* | 12/2012 | Najafi ................... | A61B 5/685 |
|              |     |         |               | 607/116    |
| 2013/0313130 | A1  | 11/2013 | Little et al.  |            |
| 2016/0058474 | A1* |  3/2016 | Peterson ................ | A61B 5/686 |
|              |     |         |               | 600/347    |
| 2016/0228061 | A1  |  8/2016 | Källbäck et al. |           |
| 2018/0164243 | A1* |  6/2018 | Noumi ............... | A61B 5/14532 |
| 2019/0357827 | A1* | 11/2019 | Li ...................... | A61B 5/14503 |
| 2020/0297239 | A1* |  9/2020 | Olson ................. | A61B 5/4839 |
| 2020/0367757 | A1* | 11/2020 | Ting ................... | A61B 5/0537 |
| 2020/0391027 | A1  | 12/2020 | Thakkar et al. |            |
| 2023/0320629 | A1  | 10/2023 | Seidl et al.   |            |

* cited by examiner

FIG. 1A                    FIG. 1B

SENSOR CANNULA

CROSS-REFERENCE TO RELATED APPLICATION(S)

The present application claims priority to and the benefit of U.S. Provisional Patent Application No. 63/592,067, filed Oct. 20, 2023, the contents of which are hereby incorporated by reference in their entirety.

BACKGROUND

Field

The present disclosure relates to sensors that are integrally formed or otherwise formed with apparatuses for delivering medication or other payloads, e.g. cannulas, that are intended to be applied to a body of a subject, and devices incorporating such sensor combinations. In some cases, the sensors may measure analytes, such as glucose, in the body of the subject, and the delivery cannulas may provide insulin. The present disclosure further relates to methods of manufacturing and methods of using such devices.

Description of Related Art

Monitoring different analytes in the human body can be used for various diagnostic reasons. In particular, monitoring glucose levels is important for individuals suffering from type 1 or type 2 diabetes. People with type 1 diabetes are unable to produce insulin or produce very little insulin, while people with type 2 diabetes are resistant to the effects of insulin. Insulin is a hormone produced by the pancreas that helps regulate the flow of blood glucose from the bloodstream into the cells in the body where it can be used as a fuel. Without insulin, blood glucose can build up in the blood and lead to various symptoms and complications, including fatigue, frequent infections, cardiovascular disease, nerve damage, kidney damage, eye damage, and other issues. Individuals with type 1 or type 2 diabetes need to monitor their glucose levels in order to avoid these symptoms and complications.

Analyte monitors, and in particular, glucose monitors for the monitoring of glucose levels for the management of diabetes, are constantly being developed and improved. Although there are several platforms for monitoring analytes such as glucose available on the market, there is still a need to improve their precision, wearability, and accessibility to end-users. In addition, there is a desire to provide robust, less painful, less error-prone, and/or generally more effective continuous glucose monitors which may be attached to the patient's body for a more prolonged period of time, as well as glucose monitor features that can be used together with such improved applicators and applicator designs.

Many diabetic patients also require delivery of medication such as insulin, based on their blood glucose readings from such monitors, in order to help regulate the flow of blood glucose from the bloodstream into the cells. Traditionally, insulin delivery is performed and regulated via an insulin pump that is separate from a glucose monitor.

SUMMARY

Many continuous glucose monitors are intended to be worn on a patient's skin for a duration of multiple days or weeks. Most or all commercially available glucose sensors on the market today sense glucose in interstitial fluid (ISF)

below the surface of the skin. Such sensing or monitoring therefore typically involves an initial step of inserting a sensor of the glucose monitor under the patient's skin. For the most part, this insertion step will involve puncturing the surface of the skin, for example, with a separate needle, for example, on an applicator to provide access for inserting the sensor. In addition, continuous glucose monitors may include a device body that remains adhered to the patient for a prolonged period of time as well.

Often, such monitors may be used in conjunction with a separate insulin delivery device, such as an insulin pump, which provides insulin in amounts determined by the glucose levels in the blood sensed by the monitors. Insulin, or other therapeutic agents, may be introduced via a hollow delivery cannula, which is typically also inserted under the patient's skin at a different site from the sensor.

Embodiments of the invention are directed to a sensor that is either formed as a hollow cannula element as an integrated device, or that is integrally formed onto a hollow cannula element, or similarly structured, such that the sensor can also be used as an insulin delivery device, thereby only requiring a single insertion point for both the sensor and insulin delivery. Such embodiments may also be used to deliver other therapeutic agents. Embodiments of the invention are further directed to devices with combined glucose sensing and insulin delivery capabilities that utilize such an integrated sensor, and methods of manufacture and/or methods of use of such devices.

According to an embodiment of the invention, a sensor assembly includes a body having a first end, a second end, and a longitudinal axis extending between the first and second ends, wherein at least part of the body is tubular and defines a cavity that extends along the longitudinal axis to facilitate delivery of medication therethrough, and a plurality of electrodes formed on a surface of the body, wherein each of the electrodes extends at least partially longitudinally along the body, with an electrical contact closer to the first end and a sensing region closer to the second end.

The plurality of electrodes may include two or more electrodes, or in other embodiments may include three or more electrodes.

At least two of the plurality of electrodes may extend substantially parallel to one another along the body.

At least two of the plurality of electrodes may have different lengths from one another.

The plurality of electrodes may all be formed on an outwardly facing surface of the body.

The electrodes may be formed on a flat substrate, where the flat substrate may be configured to be bent to form the tubular portion of the body. Opposing sides of the flat substrate may be connected to one another in the longitudinal direction to form the tubular portion of the body, such that at least part of the plurality of electrodes may extend substantially parallel to the longitudinal axis. In other embodiments, the flat substrate may be bent in a spiraling manner to form the tubular portion of the body, such that at least part of the plurality of electrodes may extend at least partially circumferentially around the longitudinal axis.

A protrusion may be formed at the second end of the body, against which an end of at least one of the plurality of electrodes may be configured to abut.

An end of at least one of the plurality of electrodes may be spaced apart from the second end of the body by at least 4 mm.

The sensor assembly may further include an additional membrane or layer formed over at least part of the plurality of electrodes, such that the at least part of the plurality of electrodes may be covered by the additional membrane or layer.

The electrodes may be fabricated on the body via a deposition process.

The body may be of sufficient rigidity to puncture a surface of a patient's skin.

According to another embodiment of the invention, a drug delivery device includes a housing configured to adhere to the skin of a patient, a compartment in the housing for holding the drug, a delivery cannula configured to extend from the housing into the skin of the patient for delivering the drug into the body of the patient, and a plurality of electrodes formed on a surface of the delivery cannula, wherein at least part of each of the plurality of electrodes is configured to extend into the skin of the patient for determining an analyte concentration associated with the patient.

The electrodes may be configured to determine a concentration of glucose associated with the patient, and the drug to be delivered may include insulin.

The drug delivery device may further include a pump for moving the drug from the compartment through the delivery cannula and into the patient's body.

The plurality of electrodes may be utilized as part of a continuous glucose monitor integrally formed with the drug delivery device.

The plurality of electrodes may all be formed on an outwardly facing surface of the delivery cannula, while the drug may be configured to be delivered through an internal cavity defined by the cannula.

The delivery cannula may be of sufficient rigidity to puncture a surface of the patient's skin.

BRIEF DESCRIPTION OF THE DRAWINGS

Further features and advantages of the invention will become apparent from the description of embodiments by means of the accompanying drawings. In the drawings.

DETAILED DESCRIPTION

In the following detailed description, only certain embodiments of the subject matter of the present disclosure are described, by way of illustration. As those skilled in the art would recognize, the subject matter of the present disclosure may be embodied in many different forms and should not be construed as being limited to the embodiments set forth herein.

Figure 1:
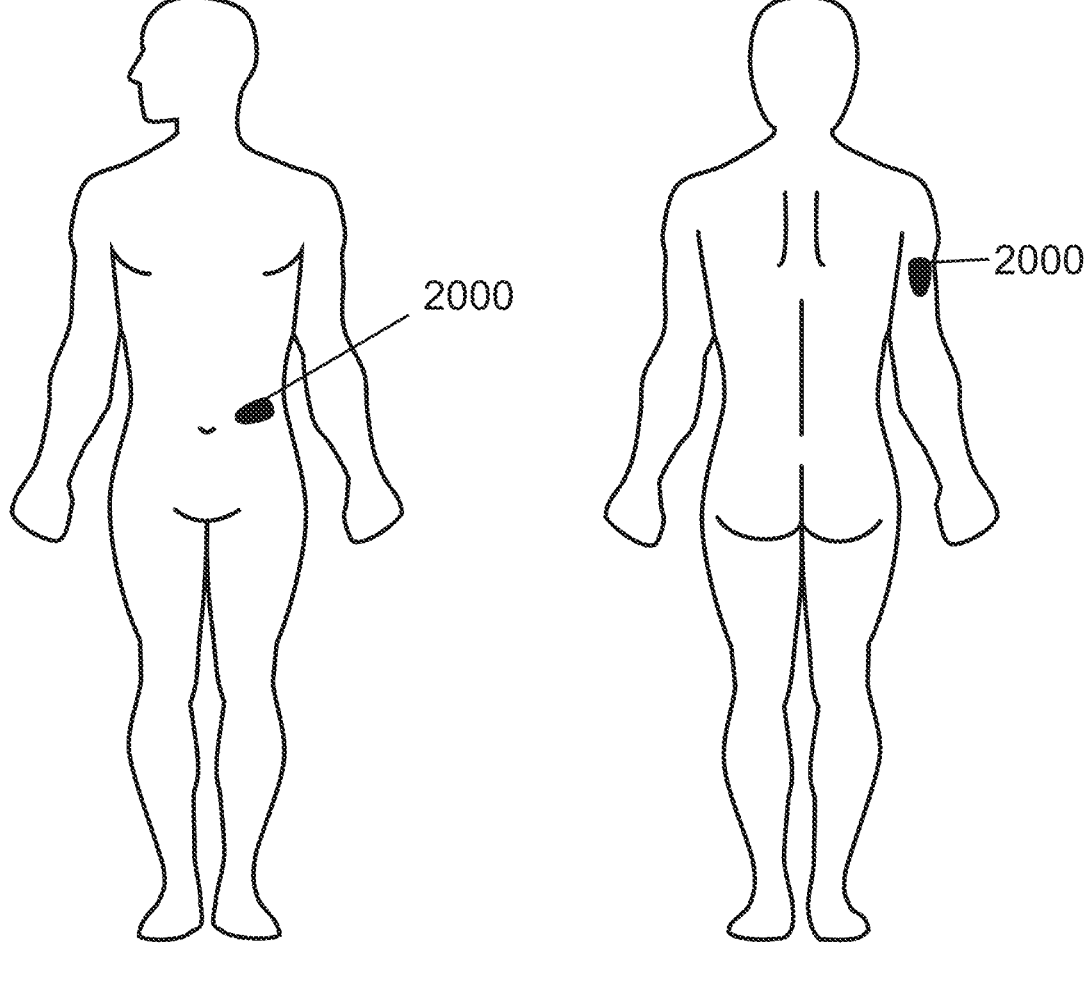
FIGS. 1A and 1B schematically show a human body with a monitor including an analyte sensor according to embodiments of the invention, where the monitor is attached at different positions on the body.

Monitors that include analyte sensors, such as glucose monitors, and particularly continuous glucose monitors, can be attached to a patient's body in different locations, in order to for example, improve glucose monitoring and/or a patient's comfort, since the continuous glucose monitors must remain adhered to the patient's skin, sometimes for a few days or more. FIG. 1A shows a first exemplary analyte monitor 2000 that is adhered to a patient's abdominal region, while FIG. 1B instead shows the exemplary analyte monitor 2000 adhered to a patient's arm. These are only meant to be example adhesion sites, and in other situations, this or a similar analyte monitor may instead be adhered or otherwise attached to other parts of the patient's body.

In cases where a patient needs both a glucose monitor and a separate insulin pump, two separate devices may need to be adhered to a patient's skin, which may involve the use of two different application sites, two separate needle punctures, additional steps to manage a patient's therapy, the need to track expirations of two separate wearables, and potential wireless communication issues between the devices since insulin delivery may be dependent on the readings from the glucose monitor, which may lead to inaccurate delivery of insulin or other medications required by the patient. Integrating the glucose monitor and insulin pump into a single device with a combined sensor and delivery mechanism would alleviate the above issues, reduce cognitive load on the patient, and also reduce the overall cost of therapy for the patient. Patients would no longer have to wear two separate devices, perform two separate insertions and two separate needle sites, or monitor expirations of two separate devices that are being used at the same time, among other inconveniences, which would also reduce pain, effort, and health risks to the patient, due at least in part to the reduction in parts and application steps to manage a patient's therapy.

Figures 2, 3:
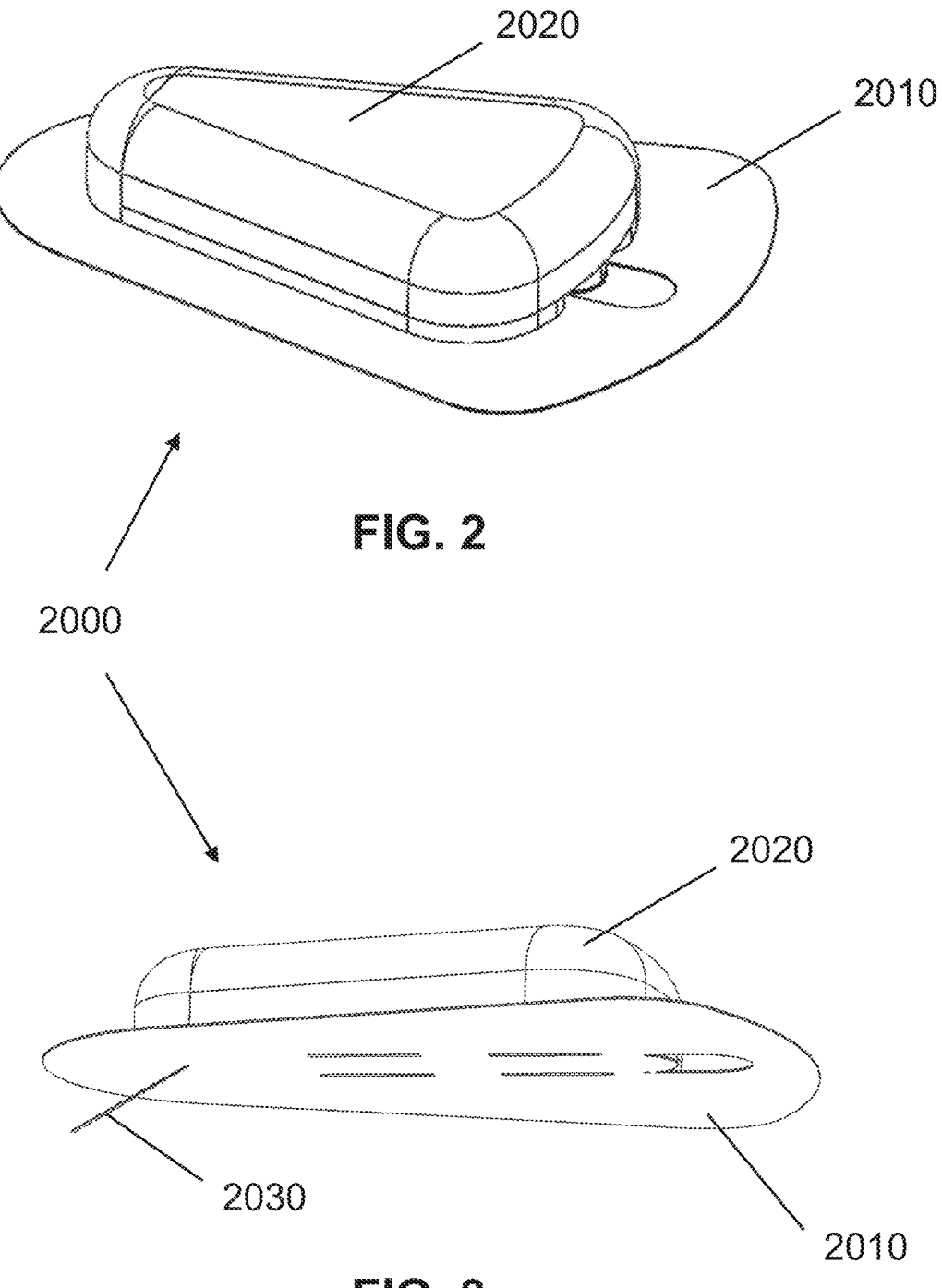
FIG. 2 shows a perspective view from above an exemplary monitor including an analyte sensor according to embodiments of the invention.
FIG. 3 shows a perspective view from below the monitor of FIG. 2.

FIGS. 2 and 3 show different schematic views of an example analyte monitor 2000, which can be a continuous glucose monitor, according to an embodiment of the invention. The continuous glucose monitor 2000 may include a base or cradle 2010 that may have an adhesive layer for adhering to a patient's skin, a transmitter 2020 for transmitting data to and/or from a location away from the monitor, and a sensor member 2030 which may include an integrated analyte sensing region such as a glucose sensor. It is to be understood that the example analyte monitor shown in FIGS. 2 and 3 are for illustrative and descriptive purposes only, and that analyte monitors with different structures and functionality can also be used in conjunction with the sensor assemblies described below, without departing from the spirit or scope of the invention.

In some embodiments, the device 2000 may also include an insulin delivery mechanism, for example, an insulin reservoir and pump, to deliver insulin to the patient. To this effect, the sensor member 2030 may be shaped or otherwise configured to facilitate delivery of insulin or one or more other therapeutic agents to the patient. In some embodiments, the sensor member 2030 may therefore be tube-shaped or cannula-shaped, so as to provide a central pathway for one or more therapeutic agents to be delivered through.

Figure 4A:
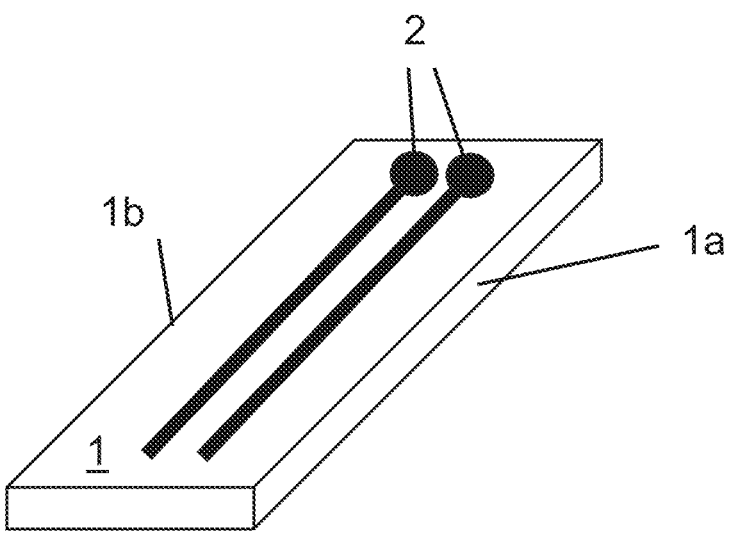
FIG. 4A schematically shows an illustrative embodiment of a substantially flat substrate with electrodes before being formed into a cannulated sensor assembly, and FIGS. 4B and 4C schematically show two alternative illustrative embodiments of sensor assemblies which have been formed into cannulated or tubular structures capable of delivering medication therethrough, according to embodiments of the invention.

FIG. 4A shows a sensor assembly prior to forming it into a cannulated member, according to an embodiment of the invention. The sensor assembly can be formed on a substrate 1. Substrate 1 can be made of or include a material that supports batch processing of electrode deposition, such as photo lithographic techniques, and/or is formable in such a way that the substrate 1 can be bent into the form of a hollow structure of a size suitable for insertion into the skin of a patient. In preferred embodiments, the substrate 1 may satisfy both of the aforementioned traits. One suitable material that can be batch processed for metal deposition is polyimide, but various other suitable materials can be used as well. Polyimide structures can be folded into tubular structures with substantially circular cross-sections with a size corresponding, for example, to 24 to 30 gauge needles. In other embodiments, the sensor assembly may be formed into a tubular structure on the order of 6 mm to 12 mm long and/or 0.3 mm to 0.7 mm in diameter. Tubular structures that are longer or shorter and that have wider or narrower cross-sections can also be formed, depending on desired functionality, drug delivery requirements, and the particular needs of each patient and case. In embodiments where substrate 1 is produced using batch processing techniques, the substrate 1 may initially be formed to be flat, or nearly so, prior to bending or otherwise molding into a desired final shape.

As further shown in FIG. 4A, electrodes 2 can be formed on substrate 1. There may be two or more electrodes 2, grouped and electrically connectable as appropriate for an appropriate sensing function. For glucose sensing, three electrodes 2 may be employed, for example, but in other embodiments with glucose sensing, more or less electrodes may be used. The electrodes 2 may include contacts to facilitate connection to further electronics housed in a glucose monitor to which the sensor assembly is attached.

Figure 4B:
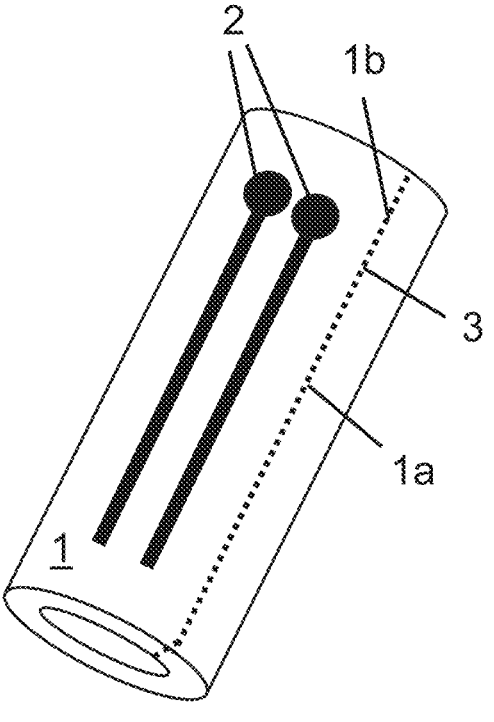
Figure 4C:
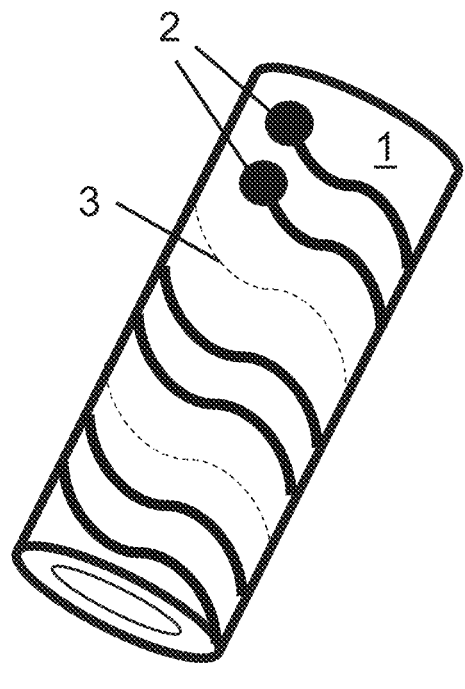

FIGS. 4B and 4C show two different embodiments for forming substrate 1 into a hollow structure. In FIG. 4B, substrate 1 is folded around an axis that runs parallel to the electrodes 2, such that outside edges 1a and 1b of substrate 1 come together and meet along seam 3, forming a body shaped as a rounded cross-sectioned hollow structure, with a substantially cylindrical cavity defined therein and with electrodes 2 located on one surface of the substrate 2. In most embodiments, the substrate 1 is folded such that the electrodes are on the outer surface of the hollow structure, but in some embodiments, folding the substrate such that the electrodes 2 are located on the inner surface of the hollow structure is also possible. Seam 3 can be sealed together using any of various known techniques, such as with laser welding or other suitable techniques. After the seam 3 is sealed or otherwise connected, the sensor assembly includes sensing electrodes 2 for glucose monitoring, and also structurally forms a hollow cannulated or tubular structure to facilitate delivery of a medical agent such as insulin, thereby incorporating both a sensor and a drug delivery device into a single structural component.

Alternative folding and sealing approaches are also possible, for example, as shown in FIG. 4C, where substrate 1 is wrapped around a central axis in a spiral or helical fashion to form the hollow structure. In the embodiment shown in FIG. 4C, seam 3 can be sealed similarly to the embodiment in FIG. 4B, or there may be an overlap between edges, and the material may be rigid enough that the form of the hollow structure will hold without a seam sealing step. The embodiment in FIG. 4C may require a more elongate substrate due to the winding nature of the configuration, whereas the embodiment in FIG. 4B may be shorter but thicker in comparison.

In some embodiments, after bending the sensor assembly into a cannulated structure, the sensor assembly may be sufficiently rigid to act as a puncturing needle, which can be advanced by itself into a patient's skin. In other embodiments, the sensor assembly may not be formed as a needle, and/or may still retain some flexibility, in which case a separate needle, for example, on an applicator device, may be required to deliver the sensor under the patient's skin, before the separate needle is removed. In either case, embodiments of the invention provide a single component that is capable of functioning as both a delivery cannula capable of dispensing medication such as insulin, and a glucose sensor capable of subcutaneous or dermal sensing of biological analytes in a patient's interstitial fluid.

Although the aim of the present disclosure is to provide both a sensor and delivery cannula for glucose monitoring and treatment, the techniques disclosed herein can apply to any situation where a cannula and a sensor can be manufactured together into a dual use structure.

Figure 5:
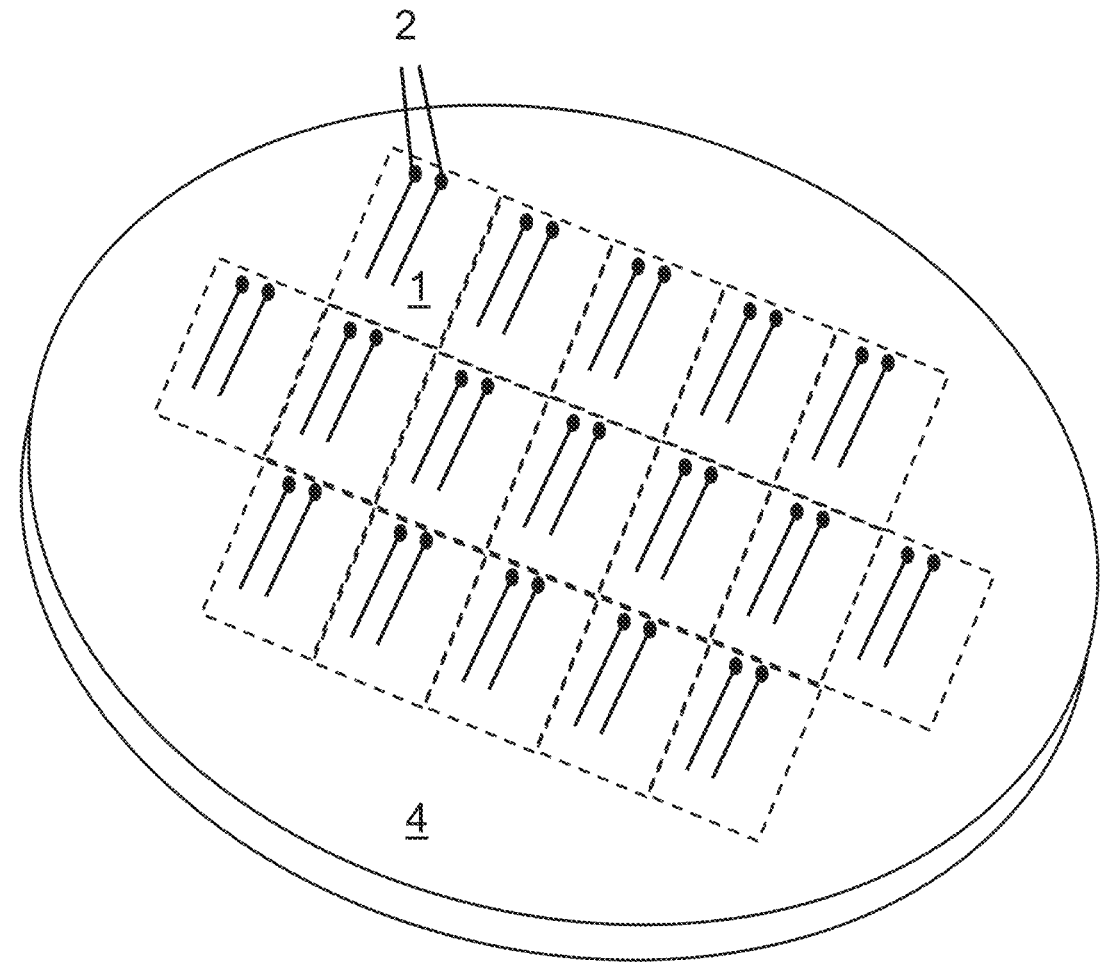
FIG. 5 schematically illustrates a batch processing approach to producing substrates that can be formed into cannulated sensor assemblies according to embodiments of the invention.

If the substrates are batch processed, for example, as illustrated in FIG. 5, and the dual use structures are produced from one substrate or wafer, the cost benefits can be substantial. For example, as shown in FIG. 5, substrates 1 with electrodes 2 may be processed in batches, using a base such as a polyimide wafer 2, and by depositing metal electrodes using, for example, photolithographic techniques or any other suitable deposition techniques. Additional layers, as will be described later, may further be applied with spin coating or any other suitable deposition techniques. Thereafter, the individual substrates 1 which are used to form each individual sensor assembly may be singulated as single die using known techniques, such as laser cutting, dicing saws, or any other suitable separation techniques. The resulting substrates 1 may then be folded or bent, and sealed if necessary, resulting in a very cost-effective solution for manufacturing a single assembly that can provide both sensing and medical agent conveyance.

Figure 6:
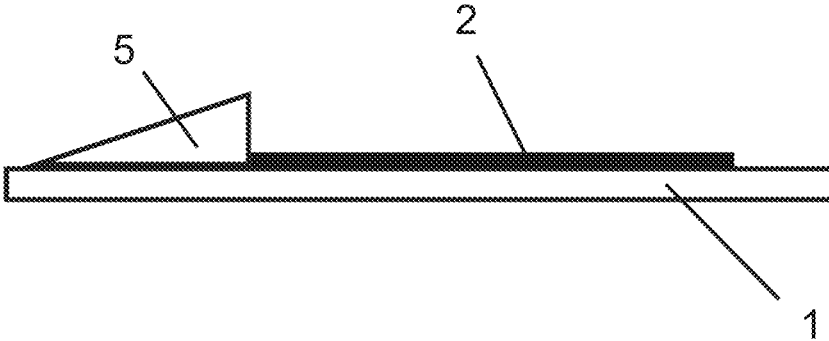
FIG. 6 schematically shows an illustrative embodiment of a structural element configured to protect the electrodes on a substrate, according to an embodiment of the invention.

Another embodiment of the invention is shown in FIG. 6. Particularly for glucose sensing, it may be advantageous to have the electrodes end a distance from the distal end of the sensor assembly after the sensor assembly has been formed, typically a minimum of 1 mm, and preferably at least 4 mm from the tip of the sensor assembly. Thus it may be advantageous to add a protrusion 5 or other small feature at the distal end of the substrate 1, to ensure an adequate spacing of the electrodes 2 from the distal end of the substrate 1, and/or to help block or otherwise protect the end of the electrode, to help prevent or reduce electrode abrasion or other damage during insertion, for example, via a traditional infusion set introduction. Such a protrusion may be created in a variety of ways, including additional photolithography on a wafer, an additional bending of the substrate, or any of various other methods. The shape of the protrusion can also take a variety of forms, as long as the result is an adequate spacing from the distal end of the sensor assembly and thereby a lessening of electrode abrasion during insertion. In the embodiment shown in FIG. 6, the protrusion 5 is formed as a tapered region that narrows towards the distal end of the substrate 1, which may facilitate easier insertion of the sensor assembly after it has been formed. However, other shapes may also be contemplated, for example, a bump or rounded bulb, to reduce agitation of the surrounding tissue by the sensor assembly. Other protective shapes may also be incorporated, such as one or more small ribs or wedges just below or proximal to the sensing region. In some embodiments, polymerized phenol may be used at the distal tip of the sensor assembly or cannula for electroreduction.

Figure 7:
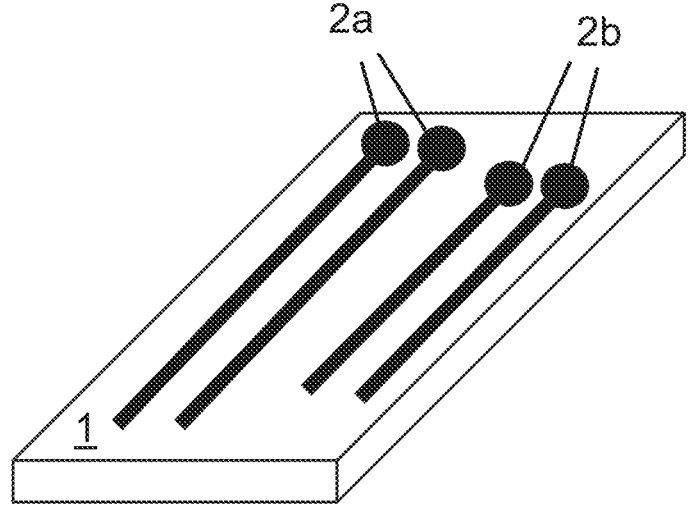
FIG. 7 schematically shows an illustrative embodiment of a substrate with a first set of electrodes having a first length and a second set of electrodes having a different second length, according to an embodiment of the invention.

As shown in FIG. 7, in some embodiments, it is possible to have more than one set of electrodes on an individual substrate 1. This may be desirable, for example, where electrodes are needed to measure different analytes, or simply for redundancy, among other reasons. In the embodiment shown in FIG. 7, there is a first pair of electrodes 2a and a separate second pair of electrodes 2b. In other embodiments, there may be more or less sets of electrodes, for example, three or more sets of electrodes, and each set of electrodes may include more or less electrodes, for example, three or more electrodes per set. In yet other embodiments, one set of electrodes may include a different number of electrodes than another set of electrodes, for example, where there is one set having two electrodes and another set having three electrodes. It is also possible for each electrode set to have different lengths, or even for individual electrodes to vary in length. Various other arrangements are also possible, depending on the desired functionality of the particular sensor and on patient needs. In still other embodiments, one set of electrodes may be formed on one side of the substrate 1, while another set of electrodes may be formed on the opposite side of the substrate 1, such that once the sensor assembly is formed into a delivery cannula, some electrodes may be on the outer surface of the sensor assembly while other electrodes may be on the inner surface of the sensor assembly.

Figure 8:
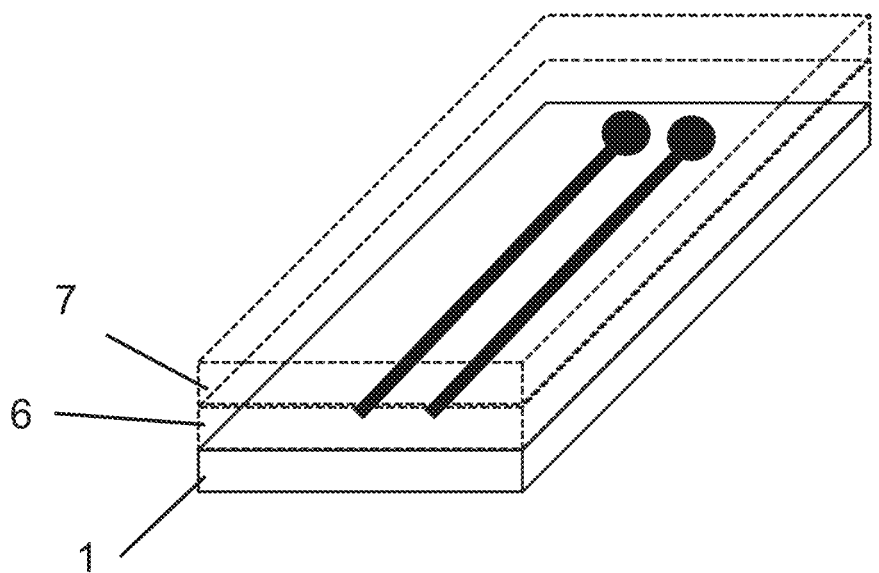
FIG. 8 schematically shows an illustrative embodiment of additional layers that can be coated onto the substrate and electrodes of a sensor, according to an embodiment of the invention.

As shown in FIG. 8, various coatings may further be applied to cover all or part of the electrodes on a substrate. In some embodiments, to facilitate glucose sensing, a biologically functional or other functional membrane or other coating layer 6 to enable electrochemistry around the electrodes may be deposited. In some embodiments, a further permeable layer or membrane 7 to reduce the rate of such reactions may be employed as well. These types of additional layers may be fully compatible with the batch processing, singulation, and forming steps disclosed herein. Any of various other coatings or other functional, protective, or other layers may also be incorporated into the sensor assembly design without departing from the spirit or scope of the invention.

In addition to the embodiments that have already been described above, it is also possible to combine embodiments, e.g., different features from the various described embodiments, to provide even more different variations of delivery cannulas and sensor electrodes without departing from the spirit or scope of the invention. In addition, the inventions should not be limited to the structures and/or shapes described in the embodiments above.

Unless otherwise defined, all terms (including technical and scientific terms) used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and/or the present disclosure, and should not be interpreted in an idealized or overly formal sense, unless expressly so defined herein.

While the subject matter of the present disclosure has been described in connection with certain embodiments, it is to be understood that the subject matter of the present disclosure is not limited to the disclosed embodiments, but, on the contrary, the present disclosure is intended to cover various modifications and equivalent arrangements included within the spirit and scope of the appended claims, and equivalents thereof.

What is claimed is:

1. A sensor assembly comprising:
a body having a first end, a second end, and a longitudinal axis extending between the first and second ends, wherein at least a portion of the body is tubular and defines a cavity that extends along the longitudinal axis to facilitate delivery of a drug therethrough; and
a plurality of electrodes formed on a surface of the body, wherein each of the plurality of electrodes extends at least partially longitudinally along the body, with an electrical contact closer to the first end and a sensing region closer to the second end; and
a protrusion formed at the second end of the body against which an end of at least one of the plurality of electrodes is configured to abut, such that the entire protrusion is positioned closer to the second end of the body than the end of the at least one of the plurality of electrodes is to the second end of the body.

2. The sensor assembly of claim 1, wherein the plurality of electrodes comprises two to four electrodes.

3. The sensor assembly of claim 1, wherein the plurality of electrodes comprises three or more electrodes.

4. The sensor assembly of claim 1, wherein at least two of the plurality of electrodes extend substantially parallel to one another along the body.

5. The sensor assembly of claim 1, wherein at least two of the plurality of electrodes have different lengths from one another.

6. The sensor assembly of claim 1, wherein the plurality of electrodes are all formed on an outwardly facing surface of the body.

7. The sensor assembly of claim 1, wherein the plurality of electrodes are formed on a flat substrate, and wherein the flat substrate is configured to be bent to form the tubular portion of the body.

8. The sensor assembly of claim 7, wherein opposing sides of the flat substrate are connected to one another in the longitudinal direction to form the tubular portion of the body, such that at least part of the plurality of electrodes extend substantially parallel to the longitudinal axis.

9. The sensor assembly of claim 7, wherein the flat substrate is bent in a spiraling manner to form the tubular portion of the body, such that at least part of the plurality of electrodes extend at least partially circumferentially around the longitudinal axis.

10. The sensor assembly of claim 1, wherein an end of at least one of the plurality of electrodes is spaced apart from the second end of the body by at least 4 mm.

11. The sensor assembly of claim 1, further comprising an additional membrane or layer formed over at least part of the plurality of electrodes, such that the at least part of the plurality of electrodes is covered by the additional membrane or layer.

12. The sensor assembly of claim 1, wherein the body is of sufficient rigidity to puncture a surface of a patient's skin.

13. The sensor assembly of claim 1, wherein the electrodes are fabricated on the body via a deposition process so as to be integrally formed on the body.

14. A drug delivery device comprising:

a housing configured to adhere to the skin of a patient:

a compartment in the housing for holding the drug; and the sensor assembly of claim 1, wherein the body of the sensor assembly forms a delivery cannula configured to extend from the housing into the skin of the patient for delivering the drug into the patient, wherein at least part of each of the plurality of electrodes is configured to extend into the skin of the patient for determining an analyte concentration associated with the patient.

15. The drug delivery device of claim 14, wherein the plurality of electrodes are utilized as part of a continuous glucose monitor integrally formed with the drug delivery device.

16. The drug delivery device of claim 14, wherein the plurality of electrodes are all formed on an outwardly facing surface of the delivery cannula, while the drug is configured to be delivered through an internal cavity defined by the cannula.

17. The drug delivery device of claim 14, wherein the delivery cannula is of sufficient rigidity to puncture a surface of the patient's skin.

\* \* \* \* \*